(12) United States Patent
Vodermayer et al.

(10) Patent No.: US 8,177,838 B2
(45) Date of Patent: May 15, 2012

(54) ARTIFICIAL HEART

(75) Inventors: Bernhard Vodermayer, Gilching (DE); Thomas Schmid, Starnberg (DE)

(73) Assignee: Deutsches Zentrum fur Luft-und Raumfahrt e.V. (DE)

( * ) Notice: Subject to any disclaimer, the term of this patent is extended or adjusted under 35 U.S.C. 154(b) by 375 days.

(21) Appl. No.: 12/309,497

(22) PCT Filed: Jul. 27, 2007

(86) PCT No.: PCT/EP2007/057774
§ 371 (c)(1),
(2), (4) Date: Nov. 18, 2009

(87) PCT Pub. No.: WO2008/012366
PCT Pub. Date: Jan. 31, 2008

(65) Prior Publication Data
US 2010/0082099 A1 Apr. 1, 2010

(30) Foreign Application Priority Data
Jul. 27, 2006 (DE) .......................... 10 2006 035 548

(51) Int. Cl.
*A61M 1/10* (2006.01)
(52) U.S. Cl. ....................................... 623/3.26

(58) Field of Classification Search ........ 623/3.13–3.28; 600/16–18
See application file for complete search history.

(56) References Cited

U.S. PATENT DOCUMENTS

| | | | |
|---|---|---|---|
| 4,922,910 A * | 5/1990 | Kanai et al. | 600/374 |
| 5,324,323 A | 6/1994 | Bui | 607/119 |
| 6,050,932 A | 4/2000 | Franchi | 600/16 |

FOREIGN PATENT DOCUMENTS

| | | |
|---|---|---|
| EP | 0 583 012 A1 | 2/1994 |
| WO | 03/068292 A1 | 8/2003 |
| WO | 2004/078234 A2 | 9/2004 |
| WO | 2008/012336 A1 | 1/2008 |

OTHER PUBLICATIONS

International Search Report dated Dec. 5, 2007 from PCT/EP2007/057774.

* cited by examiner

*Primary Examiner* — William H. Matthews
(74) *Attorney, Agent, or Firm* — Ohlandt, Greeley, Ruggiero & Perle, LLP

(57) ABSTRACT

The disclosure relates to an artificial heart implant comprising a blood pump with a pump drive, a controller for controlling and regulating the pump drive, and an electrode that is connected to the controller and is used for detecting electrical quantities on the patient's heart. The controller controls the pump drive in accordance with the signals detected by the electrode.

5 Claims, 2 Drawing Sheets

ARTIFICIAL HEART

BACKGROUND

1. Field of the Disclosure The disclosure refers to an artificial heart comprising a blood pump with a pump drive and a control for controlling and regulating the pump drive.

2. Discussion of the Background Art

In the present context, an artificial heart is to comprise all intra- and extracorporeal artificial hearts that are provided with a blood pump, i.e. extracorporeal, fully or partly implantable artificial hearts, cardiac assist systems and the like. Known artificial heart implants operate at a fixed pumping frequency or include a simple sensor system that detects and controls or regulates the motor current or the filling of the pumping chamber. Extracorporeal artificial hearts derive ECG signals exteriorly from the skin of a patient, which signals are rather weak and inaccurate due to the distance from the heart. Intracorporeal artificial hearts derive the necessary delivery rates from the motor current, the blood flow and similar parameters. These methods are limited in their accuracy and they are unreliable.

DE 697 31 848 T2 discloses a cardiac assist system controlled by means of ECG electrodes.

DE 693 22 562 T2 discloses a muscle stimulation arrangement wherein an electrode probe in the vicinity of a patient's heart is used to lead ECG signals.

It is an object of the disclosure to provide an artificial heart that is simple to implant and permanently provides good electrode signals.

SUMMARY

According to the disclosure, an electric sensor connected with the control is provided to detect electric values immediately at a patient's heart. The control controls the pump drive in dependence on the signals detected by the sensor.

The sensor may be formed by one or a plurality of ECG electrodes and/or one or a plurality of impedance electrodes. Thus, important physiologic parameters are detected that indirectly yield information about the physiologically required blood volume flow. This information is obtained, in particular, via the ECG electrodes placed or adapted to be placed immediately at a patient's heart, which detect myocardially evoked signals with high accuracy in detail. In this context, it is assumed that the cardially evoked signals are still present and accurately represent the physiological need of blood.

Because of the immediate proximity of the deriving point to the patient's heart, an ECG signal is obtained that is very detailed and allows for a precise control and regulation of the artificial heart. Besides a precise control of the blood pump or the pump drive, using the information obtained through the sensor or sensors also allows for a permanent monitoring of the patient's circulation or the patient's heart.

A blood line of the artificial heart implant is provided with one or a plurality of electrodes. The hose-like blood line has one or a plurality on its outside. The electrodes are rather large and are arranged as rings, for example, on the outer side of the blood line.

The signal lines connecting the electrodes with the control are located in or at the sheath of the blood line. Thus, the signal lines are quite well protected against excessive movements, bending or kinking.

According to a preferred embodiment, the signal line or the signal lines is/are helically provided in or at the blood line sheath. Thereby the minimum bending radii of the signal lines are very large so that the risk of line ruptures is low even in the long term.

Preferably, an electric module is provided between the electrode and a control computer, at least one short-circuit line bypassing the electric module and being directly connected with the control computer. The electric module may be an amplifier and/or a filter and/or an A/D converter. When the module or the series-connected modules are operated appropriately, the electrode signal successively passes all electrode modules in order to then be supplied to the control computer in an amplified, filtered and digitalized state. Via the short-circuit line or the short-circuit lines, the same electrode signal can be supplied directly to the control computer, bypassing one, a plurality or all of the electric modules. The control computer can continuously compare the signal on the short-circuit line with a signal coming from the last electric module. Thereby, a redundancy is achieved that guarantees the operational safety that is essential to a vital implant such as an artificial heart.

The following is a detailed description of several embodiments of the disclosure with reference to the drawings.

DETAILED DESCRIPTION OF THE PREFERRED EMBODIMENT

Figure 1:
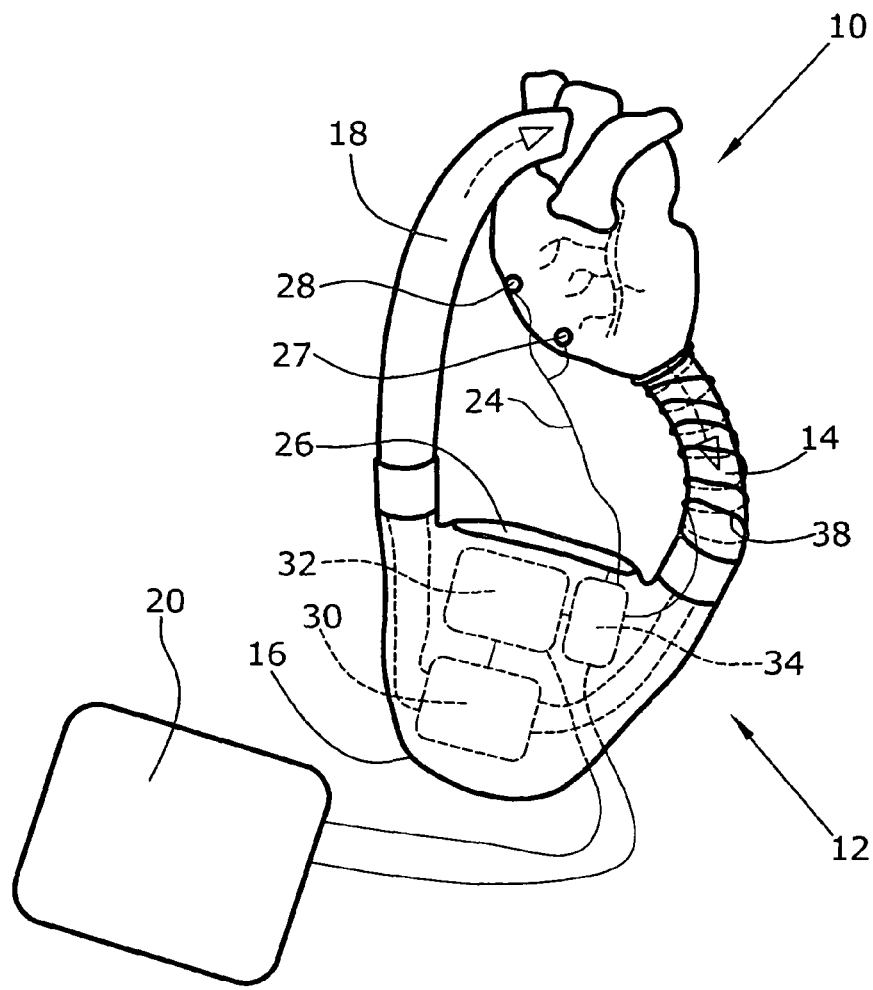
FIG. 1 is a schematic illustration of a patient's heart provided with an intracorporeal artificial heart implant.

FIG. 1 illustrates a patient's heart 10 supported by an artificial heart implant 12. The artificial heart implant 12 is a so-called full implant, i.e., it has no direct physical connection to the extracorporeal.

The artificial heart implant 12 has an inlet line 14 whose inlet side is sutured to the left ventricle of the patient's heart 10, a pump unit 16 into which the inlet line 14 opens, an outlet line 18 into which blood is pumped by the pump unit 16 and which opens into the aorta of the patient's heart 10, and an intracorporeal energy supply 20 electrically connected with the pump unit 16 through signal and data lines. The inlet and outlet lines 14, 18 are blood lines.

Further, electrodes 26, 27, 28 are arranged at the pump unit 16 and connected with the pump unit 16 via corresponding signal lines 24, which electrodes are ECG electrodes serving to lead myocardially evoked signals.

The pump unit 16 comprises a mechanical blood pump 30 supporting the patient's heart 10, the blood pump being driven by an electric pump drive 32. Further, the pump unit 16 comprises a control 34 connected, via signal and data lines, with the pump drive 32, the electrodes 26, 27, 28 as well as the energy supply 20. The control 34 controls the pump drive 32 in dependence on, among others, the ECG signal detected by the electrodes 26, 27, 28, for example, synchronous with the ECG signal. The ECG electrodes 26, 27 provided at the patient's heart 10 are sutured to the patient's heart 10.

Figure 4:
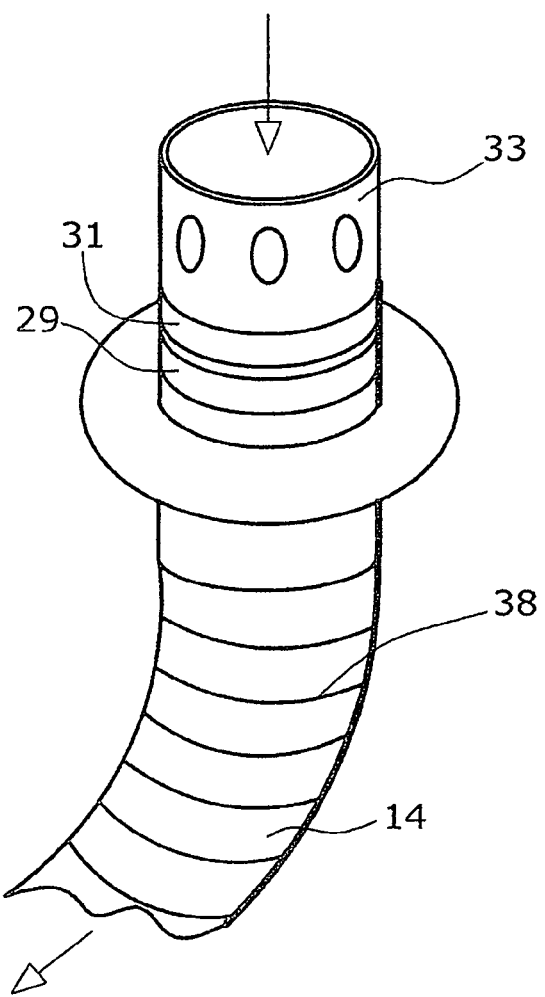
FIG. 4 illustrates another embodiment of electrodes for detecting electrical values at a patient's heart.

At the open, heart-side end of the inlet line 14, further electrodes 29, 31 are provided that are illustrated in FIG. 4. The ring electrodes 29, 31 are made of metal or an electrically conductive plastic material. The ring electrodes 29, 31 are connected with the control 34 by helical signal lines 38 placed on the hose-shaped wall of the inlet line 14.

The signal line may also be incorporated in the inlet line wall as a wire or a fabric. The signal line is insulated and is thus accommodated in the inlet line wall in a kinking- and rupture-proof manner. If a smooth basic material is used for the inlet line, e.g. silicone or PUR, the signal line may be molded into the inlet line wall. If the inlet line has a larger dimension or has a sheath, it can support and stabilize the inlet line wall and can thus protect the inlet line wall from collapsing. Instead of a helically placed signal line 38, the same may alternatively be placed axially or almost axially within the inlet line.

To ensure a good ingrowth of the distal inlet line end with the cardiac tissue, an end portion of the inlet line 14 has a velour covering 33 on the outside.

The separate ECG electrodes 27, 28 illustrated in FIG. 1 are configured as so-called fractal electrodes, i.e. they have a self-similar fractal structure, e.g. Romanesco, at their end. A high signal quality is achieved thereby. The lengths of the electrode lines 24 are fixedly predetermined. It is not possible to shorten the lines 24 during the operation. The control-side ends of the signal lines 24, 38 are provided with contact faces that are fixed in a corresponding terminal using a terminal screw and are thus connected at and with the control 34.

Depending on the desired signal type, i.e. ECG signal or impedance signal, the electrodes 27, 28 are positioned on the left ventricle in an optimum position with respect to the potential line so as to obtain an optimally evaluatable ECG signal. If it is intended to obtain an atrium ECG for determining atrial fibrillation, an electrode should also be positioned there.

For a measuring of impedance-cardiographic characteristics of the patient's heart 10, three to four electrodes must be provided, namely one or two ground electrodes 26, a signal electrode generating a signal of 150 kHz, for example, and an impedance electrode. A single ground electrode is sufficient, if a large-surface housing is used as the ground electrode.

Figure 3:
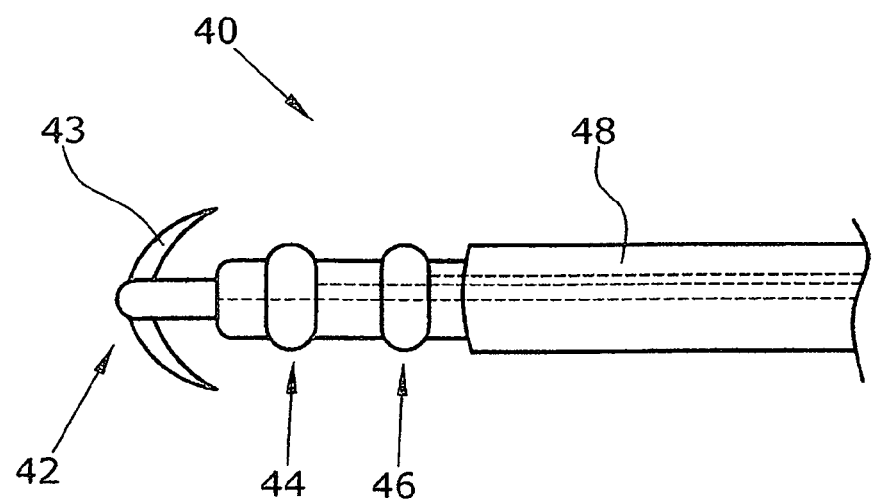
FIG. 3 is an alternative embodiment of an arrangement of electrodes at a probe for detecting electric values at a patient's heart.

FIG. 3 illustrates an electrode probe 40 useful as an alternative or a complementary means to the arrangement in FIG. 1, whose distal end has three electrodes 42, 44, 46 provided thereon. The end electrode 42 has a hook 43 which is inserted into the myocardium to which it may be sutured, for example. The two other electrodes 44, 46 are annular in shape. The maximum value of potential is defined by the mutual distance of the three electrodes 42, 44, 46. One of the electrodes 46 may form the ground electrode, fro example, while another electrode 44, 42 may form an ECG electrode.

Using corresponding insulated lines, the three electrodes 42, 44, 46 are placed in a probe sheath 48 in a kinking-proof manner. Thus, ruptures in the signal lines are avoided in the long term.

Figure 2:
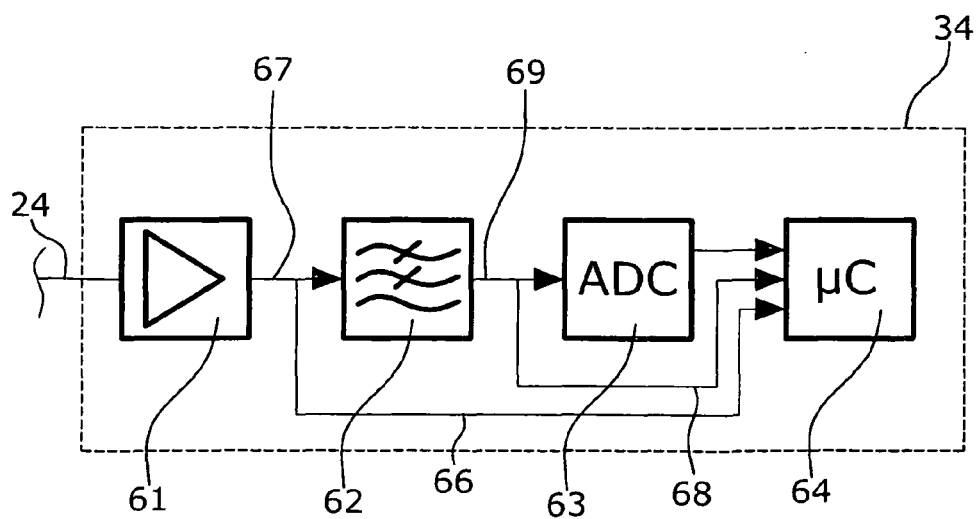
FIG. 2 is a schematic illustration of several modules of the artificial heart control of the artificial heart implant in FIG. 1.

FIG. 2 illustrates several electronic modules 61, 62, 63, 64 of the control 34, namely an amplifier module 61, a filter module 62, an A/D-converter module 63 and a control computer 64. Further, two short-circuit lines 66, 68 are provided that directly connect the signal line 67, 69 between the amplifier module 61 and the filter module 62 or between the filter module 62 and the A/D converter module 63 with the control computer 64. The control computer-side inputs for the two short-circuit lines 66, 68 are configured as A/D converters.

The analogue signals from the electrodes are supplied to the input of the amplifier module 61 via the signal lines 24. From there, the amplified signal is transmitted to the filter module 62 via the signal line 67. The electrode signal filtered by the filter module 62 is supplied to the high-resolution A/D converter module via the signal line 69. From there, the digitalized electrode signal is transmitted to a digital input of the control computer 64.

The connection of the A/D converter module(s) 63 with the control computer 64 may be established through an I²C- or a SPI-bus.

By means of the short-circuit lines 66, 68, the control computer 64 may check the processed electrode signal received by the A/D converter module 63 for extensive consistence. Further, in the event of a failure of the filter module 62 and/or the A/D converter module 63, sensor signal from the amplifier module 61 can still be used and be further evaluated, albeit in lesser quality.

Thus, a high degree of controllability and redundancy is realized using simple means. Furthermore, modules 62, 63 can thus be calibrated posteriorly.

The control 34 controls the performance of the pump drive 32 as a function of the ECG and impedance signals measured by the electrodes, e.g. in a manner synchronous with the heart beat.

The electrodes 26, 27, 28, 29, 31 that are in contact with the bloodstream may be provided with coagulation-inhibiting coatings or they may have special surfaces allowing no or only little accretion of blood plates. This also applies to the electrodes that may come into contact with blood in certain areas outside the bloodstream, in which the accretion of thrombocytes may be dangerous.

What is claimed is:

1. An artificial heart comprising:
    a blood inlet line and/or a blood outlet line,
    a blood pump with a pump drive,
    a control for controlling and regulating the pump drive, and
    an electrode connected with the control for detecting electrical values at a patient's heart, the control controlling the pump drive as a function of the electrical values detected by the electrode,
    wherein the electrode is provided at the blood inlet line or the blood outlet line, and an electrical signal line is provided between the electrode and the control in or at the wall of the blood inlet line or the blood outlet line, and
    wherein the electrode is provided in an annular shape on an outer side of the blood inlet line and/or the blood outlet line and is adapted to be placed immediately at the patient's heart.

2. The artificial heart of claim 1, wherein the electrode is an ECG electrode.

3. The artificial heart of claim 1, wherein the electrode is an impedance electrode.

4. The artificial heart of claim 1, wherein the signal line is placed helically at or in the wall of the inlet line or the outlet line.

5. An artificial heart comprising:
    a blood inlet line and/or a blood outlet line,
    a blood pump with a pump drive,
    a control for controlling and regulating the pump drive, and
    an electrode connected with the control for detecting electrical values at a patient's heart, the control controlling the pump drive as a function of the electrical values detected by the electrode,
    wherein the electrode is provided at the blood inlet line or the blood outlet line, and an electrical signal line is provided between the electrode and the control in or at the wall of the blood inlet line or the blood outlet line, and
    wherein the control comprises an electric module between the electrode and a control computer, wherein at least one short-circuit line bypasses the module and is directly connected with the control computer.

* * * * *